US011427854B2

(12) United States Patent
Guy et al.

(10) Patent No.: US 11,427,854 B2
(45) Date of Patent: Aug. 30, 2022

(54) AUTOMATED SYSTEM FOR THE LYSIS OF MICROORGANISMS PRESENT IN A SAMPLE, FOR EXTRACTION AND FOR PURIFICATION OF THE NUCLEIC ACIDS OF SAID MICROORGANISMS FOR PURPOSES OF ANALYSIS

(71) Applicant: BIOMERIEUX, Marcy L'Etoile (FR)

(72) Inventors: Michel Guy, Grenoble (FR); Hervé Rostaing, Le Versoud (FR)

(73) Assignee: BIOMERIEUX, Marcy L'Etoile (FR)

( * ) Notice: Subject to any disclaimer, the term of this patent is extended or adjusted under 35 U.S.C. 154(b) by 0 days.

(21) Appl. No.: 16/797,405

(22) Filed: Feb. 21, 2020

(65) Prior Publication Data

US 2020/0190561 A1     Jun. 18, 2020

Related U.S. Application Data

(62) Division of application No. 14/409,979, filed as application No. PCT/FR2013/051681 on Jul. 12, 2013, now Pat. No. 10,619,185.

(30) Foreign Application Priority Data

Jul. 13, 2012    (FR) ...................................... 1256758

(51) Int. Cl.
    *C12Q 1/68*     (2018.01)
    *C12Q 1/6806*   (2018.01)
    (Continued)

(52) U.S. Cl.
    CPC ........... *C12Q 1/6806* (2013.01); *C12M 47/06* (2013.01); *C12Q 1/24* (2013.01); *B01L 3/502761* (2013.01)

(58) Field of Classification Search
    USPC .......... 435/6.1, 6.11, 7.1, 91.1, 283.1, 287.1, 435/287.2; 436/94, 501; 536/23.1, 24.3;
    (Continued)

(56) References Cited

U.S. PATENT DOCUMENTS 5,454,493 A    10/1995    Laroche et al.
5,503,995 A     4/1996    Khudyakov et al.
(Continued)

FOREIGN PATENT DOCUMENTS

FR    2607507 A1    6/1988
FR    2781802 A1    2/2000
(Continued)

OTHER PUBLICATIONS

Chevalier, Jacques et al. "Biotin and Digoxigenin as Labels for Light and Electron Microscopy in Situ Hybridization Probes: Where Do We Stand?". vol. 45, No. 4, 481-491, 1997. The Journal of Histochemistry & Cytochemistry.
(Continued)

*Primary Examiner* — Frank W Lu
(74) *Attorney, Agent, or Firm* — Oliff PLC

(57) ABSTRACT

A method for collecting microorganisms when contained in a fluid includes (i) introducing the fluid into a cavity of a collecting device via at least one admission duct, (ii) capturing the microorganisms when contained in the fluid with a set of beads retained in the cavity as the fluid passes through the set of beads, (iii) evacuating the fluid from the cavity via at least one evacuating duct, (iv) introducing a reaction liquid into the cavity via at least one admission channel, (v) collecting the microorganisms from the set of beads with the reaction liquid as the reaction liquid passes through the set of beads, and (vi) evacuating the reaction liquid from the cavity via at least one evacuating channel.

14 Claims, 6 Drawing Sheets

(51) Int. Cl.
*C12Q 1/24* (2006.01)
*C12M 1/00* (2006.01)
*B01L 3/00* (2006.01)

(58) Field of Classification Search
USPC .................................................. 530/300, 350
See application file for complete search history.

(56) References Cited

U.S. PATENT DOCUMENTS

| | | | |
|---|---|---|---|
| 5,567,050 | A | 10/1996 | Zlobinsky et al. |
| 5,707,861 | A | 1/1998 | Sherman et al. |
| 9,228,352 | B2 | 1/2016 | Valentz et al. |
| 2003/0203504 | A1 | 10/2003 | Hefti |
| 2006/0094051 | A1 | 5/2006 | Lee et al. |
| 2008/0131653 | A1 | 6/2008 | Lyons et al. |
| 2008/0237134 | A1* | 10/2008 | Chang ................ B01J 20/3425 210/662 |
| 2010/0297604 | A1* | 11/2010 | Li ...................... G01N 33/56983 435/5 |
| 2011/0053187 | A1* | 3/2011 | Dao ................... G01N 33/56961 435/7.31 |

FOREIGN PATENT DOCUMENTS

| | | |
|---|---|---|
| GB | 2254024 A | 9/1992 |
| JP | 2006-129869 A | 5/2006 |
| WO | 95008000 A2 | 3/1995 |
| WO | 2004018704 A2 | 3/2004 |
| WO | 2005038025 A1 | 4/2005 |
| WO | 2008/104916 A2 | 9/2008 |
| WO | 2009001010 A2 | 12/2008 |
| WO | 2010067019 A2 | 6/2010 |
| WO | 2010133776 A2 | 11/2010 |
| WO | 2011033231 A1 | 3/2011 |

OTHER PUBLICATIONS

Egholm, Michael et al. "Peptide Nucleic Acids (PNA). Oligonucleotide Analogues with an Achiral Peptide Backbone". vol. 114, 1895-1897, 1992. J. Am. Chem. Soc.

Kumar, Ravindra et al. "The First Analogues of LNA (Locked Nucleic Acids): Phosphorothioate-LNA and 2'-Thio-LNA". vol. 8, 2219-2222, 1998. Bioorganic & Medicinal Chemistry Letters.

* cited by examiner

Detail A

AUTOMATED SYSTEM FOR THE LYSIS OF MICROORGANISMS PRESENT IN A SAMPLE, FOR EXTRACTION AND FOR PURIFICATION OF THE NUCLEIC ACIDS OF SAID MICROORGANISMS FOR PURPOSES OF ANALYSIS

This is a Divisional of application Ser. No. 14/409,979 filed Dec. 19, 2014, now U.S. Pat. No. 10,619,185 issued Apr. 14, 2020, which is a National Stage Entry of PCT/FR2013/051681 filed Jul. 12, 2013, published as WO 2014/009673 on Jan. 16, 2014, which claims priority to FR 1256758 filed Jul. 13, 2012. The disclosure of the prior applications is hereby incorporated by reference herein in its entirety.

The field of technology of the present invention is that of biological analysis. More particularly, the present invention relates firstly to a device for lysis of the microorganisms present in an environmental or clinical sample, for extraction and for purification of the nucleic acids of said microorganisms. The invention further relates to an automated system for lysis of microorganisms for extraction and purification of the nucleic acids of said microorganisms, for the purposes of analysis.

For several years there has been a considerable increase in the incidence of nosocomial infections in hospitals. These infections are explained by the contamination of the hospitalized persons, who therefore are by definition immunodepressed, by pathogenic microorganisms that are present in the hospital environment and are not destroyed despite the great care always paid to disinfection of equipment and surfaces and to air conditioning. In view of these more and more frequent cases of environmental microbiological contamination, development of devices and methods for improving and facilitating environmental controls has become a major challenge for health professionals.

Apart from the problem of nosocomial infections, monitoring of environmental conditions has over recent years been a recurrent concern in the industrial environment, in particular in the food industries and the pharmaceutical or cosmetics industries. In the food industries, we are familiar with the disastrous consequences that contamination of products, or even of raw materials, with a pathogenic microorganism may have for consumers' health. In fact, toxic food infections, due to bacteria such as those of the genus *Listeria* or *Salmonella*, are now of common occurrence. Monitoring of air quality is also a key process in the quality approach of the pharmaceutical or cosmetics industries.

Moreover, this monitoring must meet an ever increasing level of requirements, owing to increasingly stringent regulations.

Among the tools available to health professionals or manufacturers for carrying out environmental monitoring, the air biosamplers are solutions of choice for detecting microorganisms in the air. These devices are placed at suitable points in places where we wish to measure aerobio-contamination. They generally consist of an air sampler coupled to a culture medium. The air collected by the air sampler comes into contact with the culture medium; any airborne microorganisms collected will be deposited on said culture medium. The culture medium is then recovered and put in a stove to promote growth of the microorganisms. It is thus possible to detect and identify said microorganisms by traditional microbiology techniques.

These devices nevertheless have a major drawback that is associated with the technology used. This drawback is the time taken to obtain the analysis result. In fact, the use of the traditional techniques of microbiology, especially of bacteriology, involves waiting the incubation times necessary for cellular growth, or even for steps of reseeding on specific culture media to allow identification. As a result, the time taken to obtain a result is relatively long, or even too long, when we wish to detect and identify a pathogenic organism responsible for a nosocomial infection or for food poisoning.

Another drawback of this type of device is that although the use of culture media makes it possible to discriminate between genera and species of bacteria, it does not generally make it possible to discriminate between the strains of one and the same bacterial species. Now, it is known that the pathogenicity of a microorganism may vary significantly depending on the strain in question.

Moreover, this type of device has the drawback that it does not allow detection of airborne microorganisms that are viable but are not cultivatable.

These devices also have the drawback of drying of the nutrient surfaces as collection continues.

Moreover, there are devices that are intended for recovery of airborne particles, especially microorganisms. Thus, document GB-2 254 024 describes a device for collecting the particles present in the air based on the principle of the cyclone effect. Although such a device proves suitable for collecting the particles present in the air, including microorganisms, it has never been investigated for treating the sample thus obtained, in particular for carrying out extraction of the genetic material, intended to be used for analysis.

More generally, the most relevant techniques in terms of identification of microorganisms and/or of speed of delivering the results, whether with respect to clinical samples or environmental samples, are without any doubt the techniques of molecular diagnostics. These techniques, based on analysis of the genetic material of the microorganisms, and in particular of certain specific sequences of interest, make it possible to obtain very precise identification of the microorganisms in a record time, since they make it possible to omit the culture steps.

Nevertheless, the use of such techniques has a certain number of limitations, the most important of which is the potentially limited quantity of microorganisms present in the air and therefore recoverable for performing the analysis. In fact, it is known that environmental samples, but also certain clinical samples, are relatively poor in microorganisms. As a result, the amount of genetic material obtained from this raw material is small. The performance of the technique used for extracting the nucleic acids, in terms of yield, then becomes a crucial parameter.

Moreover, most of the existing techniques for lysis of microorganisms are not general with respect to all microorganisms and/or require the intervention of qualified personnel for performing the manual steps.

Document WO-A-2005/038025 describes a method for extracting nucleic acids from microorganisms notably sampled from the air. This method consists of employing three different methods of lysis, namely chemical lysis, heat shock lysis and mechanical lysis. If such a method makes it possible without any doubt to optimize the efficiency of extraction of the nucleic acids and therefore increase the amount of genetic material available for analysis, it is still the case that this efficiency remains dependent on the quantity of microorganisms recovered. Now, nothing is described in this document for optimizing the recovery of said microorganisms.

Document U.S. Pat. No. 5,707,861 describes a device for disrupting living cells such as microorganisms. This device allows cells to be lysed using both glass beads and the effect of vibration due to the space between the tubes containing the microorganisms and the holes of the support carrying said tubes. Thus, such a device makes it possible to optimize cellular lysis and therefore optimize extraction of the genetic material. Such a device and the method that it employs have the same limitations as those discussed above, namely that they remain dependent on the quantity of microorganisms recovered. Moreover, they have the additional drawback of requiring a subsequent step of concentration of the nucleic acids in order to isolate them from the cellular debris. Finally they require recovering the nucleic acids manually at the end of the concentration step.

These problems also arise with the device described in document U.S. Pat. No. 5,567,050.

Systems with greater integration have also been described. Thus, document WO-A-2004/018704 describes a device, and an associated method using the technique of PCR (Polymerase Chain Reaction) amplification, for collecting microorganisms in the air and identifying them. This system is specially designed for combating assassination attempts by biological contamination in mail sorting centers. This system consists of an air sampling device placed along the circuit for transporting the mail, a device for filtration/separation of particles by the cyclone effect, a device for concentration/recovery of particles from a liquid sample, a device for transferring a fraction of the sample into a GeneXpert™ PCR analysis cartridge from the company Cepheid in California. The cartridge is then transferred manually to an independent automatic biological analyzer for identification of the microorganism or microorganisms collected from the air.

Although this system solves a good number of technical problems associated with the devices and methods described above, it nevertheless has major drawbacks. The first of these drawbacks is that the system for sample treatment (collection, separation, concentration/recovery) prior to transfer to the analysis cartridge is relatively complex and expensive. A second drawback is that the microorganisms collected are recovered in a liquid sample, only a fraction of which is analyzed. This means that there is a considerable risk of not recovering all of the microorganisms and therefore all of the nucleic acids, which greatly limits the suitability of the analysis. Moreover, despite its complexity, this system requires manual transfer of the cartridge into the GeneXpert™ automatic analyzer.

The applicant has already filed a patent application WO-A-2009/001010 that relates firstly to a cartridge, suitable for placing inside an air sampling means and for receiving a means for recovering the nucleic acids, said cartridge, of roughly cylindrical shape, comprising a retention zone of the microorganisms, said retention zone comprising means for lysis of microorganisms. This invention further relates to a device for collecting airborne microorganisms and a device for lysis of microorganisms.

The applicant has also already filed a patent application WO-A-2010/067019 which, among other things, relates to a device for collecting airborne microorganisms, said device comprising:
  an air sampling module, comprising:
    i. an upper element comprising an air admission duct allowing entry of a stream of air into said module, said duct having, at its base, means for disturbing the air stream,
    ii. a lower element comprising means for evacuating the air, allowing exit of the air stream created it being possible for said upper and lower elements to be integrated with one another so that the air stream can be created within said air sampling module;
  a cartridge, of roughly cylindrical shape, comprising a retention zone of the microorganisms, said retention zone comprising means for lysis of microorganisms, said cartridge being positioned inside said air sampling module.

With these two novel solutions, it is undeniable that the process is improved with universal lysis, effective both for environmental and clinical samples, for a great variety of microorganisms, whether they are bacteria, viruses or fungi, optionally in the vegetative state or in the form of spores.

Moreover, there is quite a high concentration of microorganisms, the system is compatible with various downstream analyses (such as PCR, streaking on dishes, etc.), and the mechanical lysis is integrated.

However, it is not in human nature to be content with a system that functions well, when an even more optimal solution may be found. Thus, in these two instances, collection is still limited by the volume of fluid, gaseous or liquid, which comes into contact with the recovery medium, generally a culture medium. The stream of fluid will always impinge on this medium at the same point, which will lead:
  either to saturation of said medium in a precise spot without the rest being used,
  or to degradation of this medium as it is always impacted by a gas or a liquid at the same point(s), which leads to desiccation in the case of a gas and liquefaction of the surface of the medium in the case of a liquid. In both cases and notably in the case of desiccation of agar, there will be a very marked decrease in capture efficiency as a function of time.

Moreover, the manner of capture by impacting is very inefficient for small particles with a diameter of less than 1 μm. Another problem is that there is a risk of entrainment of a proportion of the recovery medium (beads with glycerol) by the air stream. Thus, this projection of fluid and its rebound on said medium may generate splashes, which are a further risk of contamination.

The aim of the present invention is to propose an apparatus that tackles the drawbacks described above.

For this, the invention proposes a device for collecting microorganisms contained in a fluid, said device comprising:
  a reaction module containing a set of beads,
  at least one fluid admission duct allowing a stream of fluid to enter the module,
  at least one duct for evacuating the fluid, allowing exit of the stream of said fluid that has passed through the interior of said module,
  means for retaining the beads inside the module,
  at least one channel for admitting at least one reaction liquid,
  at least one channel for evacuating at least one reaction liquid,
  the channels for admitting and evacuating the reaction liquid and the ducts for admission and evacuation of the fluid being positioned as follows at module level:
    the ducts for admission and evacuation of the fluid facing one another while enclosing the module, in order to maximize contacts between the fluid and the beads,
    the channels for the reaction liquid or liquids being positioned respectively at two opposite ends of the module, and
    the channels for the reaction liquid or liquids are positioned in one plane, and the ducts for admission and evacuation of the fluid are positioned along an axis, said axis being roughly perpendicular to the plane.

According to a first embodiment, the device according to the invention comprises an airtight confinement enclosure, isolating the fluid and the reaction liquids from the exterior.

According to a first embodiment of the device, if the fluid is a gas, the set of beads consists of beads coated with glycerol.

According to a second embodiment of the device, if the fluid is a liquid, the module contains a filter extending approximately in the plane formed by the channels for the reaction liquid or liquids, the admission channel(s) being positioned on one side of the filter with the set of beads and the evacuating channel(s) being positioned on the other side of said filter in the absence of beads. This arrangement thus allows the fluid to come into contact with the beads and then circulate through the filter, in order to separate for example any cellular residues that are of no interest or inhibitors, such as proteins, membranes.

In a particular embodiment, the shape of the module, if it is cut:
along the plane formed by the channels for admitting and evacuating the reaction liquid, and
perpendicularly to the axis formed by the ducts for admission and evacuation of the fluid,
comprises at least one rectilinear portion and/or at least one portion in an arc, which are comprised between two ends. The channel(s) for admission of the reaction liquid are located at one end of the module and the channel(s) for evacuating the reaction liquid are located at the other end of the module, so that the reaction liquid passes completely through the bed of beads between the moment when it is admitted into the admission channel(s) of the reaction liquid and the moment when it is evacuated via the evacuating channel(s) of the reaction liquid. According to this last-mentioned embodiment or variant, the module has a quadrilateral section if it is cut along a plane perpendicular to the plane formed by the channels for admitting and evacuating the reaction liquid, and passing along the axis formed by the ducts for admission and evacuation of the fluid.

In a particular embodiment, the module is of "C" shape if it is cut:
along the plane formed by the channels for admitting and evacuating the reaction liquid, and
perpendicularly to the axis formed by the ducts for admission and evacuation of the fluid A "C" shape comprises at least one portion in an arc corresponding to a portion of the circumference of a circle or of a parabola joining two points. The ends of the "C" being the two end zones of the module, so that the channel(s) for admission of the reaction liquid are located at one end of the module and the channel(s) for evacuating the reaction liquid are located at the other end of the module, the reaction liquid passes completely through the bed of beads between the moment when it is admitted into the admission channel(s) of the reaction liquid and the moment when it is evacuated via the evacuating channel(s) of the reaction liquid.

According to this last-mentioned embodiment or variant, the module is of quadrilateral shape if it is cut along a radius passing through the center of the "C" and cutting through said "C".

Still according to this last-mentioned embodiment or variant, the admission channel(s) of the reaction liquid is(are) located at one end of the "C" of the shape of the module, and the evacuating channel(s) of the reaction liquid is(are) located at the other end of the "C".

Regardless of the embodiment or variant, the beads have a diameter between 200 and 600 μm and the means for retaining said beads inside the module consist of grids, the pores of which have a diameter smaller than the beads and in the range from 100 to 500 μm.

Regardless of the embodiment or variant, it comprises another reaction module for treatment of the microorganisms collected, said module containing:
means for separating the cellular residues that are of no interest or inhibitors, such as proteins, membranes, and/or
means for amplification of the nucleic acids collected and separated from the inhibitors, and/or
means for detecting the amplicons thus generated.

The present invention also relates to a method for collecting microorganisms contained in a fluid, which consists of:
introducing the fluid suspected of containing microorganisms via at least one fluid admission duct,
passing through a bed of beads, where the microorganisms are immobilized,
evacuating the fluid, from which said microorganisms have been removed, via at least one duct for evacuating said fluid,
introducing at least one reaction liquid via at least one reaction liquid admission channel,
passing through the bed of beads where the microorganisms are immobilized in order to put said microorganisms in suspension, and
evacuating this liquid transporting the microorganisms via at least one channel for evacuating the reaction liquid(s),
the ducts for admission and evacuation of the fluid facing one another while enclosing the bed of beads, the channels for admitting and removing the reaction liquid(s) being positioned so as to reach all of the beads.

According to one embodiment, when the fluid is a gas, the beads are coated with glycerol.

According to one embodiment, when the fluid is a liquid, the beads are coated with a polymer coating.

According to one embodiment, when the reaction liquid passes through the bed of beads, said beads are agitated by an external agitating means and come into contact, which makes it possible to destroy or to disrupt the membranes of the microorganisms, making the nucleic acids accessible and ready to be evacuated.

According to one embodiment, a defined amount of reaction liquid is admitted into the admission channel(s) of the reaction liquid and is not evacuated via the evacuating channel(s) of the reaction liquid during lysis, so that the microorganisms are lysed for a defined time in the presence of a defined amount of reaction liquid. This time is preferably between 5 and 30 minutes and this amount of liquid is preferably between 100 μl and 1 ml, and more preferably is 500 μl.

According to a variant of this embodiment, the beads are agitated using ultrasound.

Regardless of the embodiment or variant, the liquid loaded with some or all of the microorganisms is evacuated to another reaction module of the device allowing treatment of the microorganisms collected, said treatment consisting of:
separating the cellular residues that are of no interest or inhibitors, such as proteins, membranes, and/or
amplifying the nucleic acids collected, and/or
detecting the amplicons thus generated.

Regardless of the embodiment or variant, a first possibility for this method is characterized in that:
the fluid tested consists of a gas (for example air),
the gas passes through the bed of beads, said beads being coated with glycerol, where the microorganisms are immobilized, and
at least one reaction liquid is introduced in order to liquefy the glycerol and put said microorganisms in suspension.

Regardless of the embodiment or variant, a second possibility for this method is characterized in that:
the fluid tested consists of a liquid,
the liquid tested passes through the bed of beads and then a filter before being evacuated, after removal of the microorganisms that it contained; the microorganisms are immobilized, and
at least one reaction liquid is introduced in order to put said microorganisms in suspension.

According to either one of these two possibilities, the liquid is filtered between evacuation via at least one channel for evacuating the reaction liquid and the module for removing the inhibitors and/or for amplification and/or for detection.

Fluid sample means any gaseous or liquid sample that may contain microorganisms. It may be a sample of human or animal origin. This sample may be, for example, urine, whole blood, plasma or any other body fluid or exhaled air. The sample may be of food origin such as a drink. It may also be of environmental origin, such as water or confined air. Moreover, the liquid sample may also be a so-called transfer liquid, in which any microorganisms contained on a surface sampling device, of the swab type such as those marketed by the company COPAN, under the name "flocked SWABS", have been resuspended by agitating said swab in said transfer liquid.

The microorganisms are from the group comprising bacteria, viruses, yeasts, molds, parasites.

The samples from which the microorganisms are isolated are of environmental origin. Thus, it may be a sample of air or of liquid, such as water; surface samples. The samples may also be of clinical origin, namely any sample of human or animal origin, suitable as the object of an analysis for detecting it and the identification of a microorganism, optionally pathogenic.

The presence of the target nucleic acids may be detected by visualization of hybridization reactions. Hybridization reaction means any reaction between a capture nucleic acid and a target nucleic acid isolated or generated by a step of transcription, reverse transcription or amplification, for example of the NASBA type (for Nucleic Acid Sequence Based Amplification) or PCR.

Nucleic acid means oligonucleotides, deoxyribonucleic acids and ribonucleic acids, and derivatives thereof. The term oligonucleotide denotes a sequence of at least two nucleotides (deoxyribonucleotides or ribonucleotides, or both), preferably at least five, preferably at least eight, and even more preferably at least fourteen, whether they are natural or modified, able to hybridize, in suitable hybridization conditions, to another oligonucleotide, at least partially complementary.

Modified nucleotide means for example a nucleotide comprising a modified base and/or comprising a modification at the level of the internucleotide bond and/or at the level of the skeleton. As an example of modified base, we may mention inosine, methyl-5-deoxycytidine, dimethylamino-5-deoxyuridine, diamino-2,6-purine and bromo-5-deoxyuridine.

To illustrate a modified internucleotide bond, we may mention the phosphorothioate, N-alkylphosphoramidate, alkylphosphonate and alkylphosphodiester bonds.

The alpha-oligonucleotides such as those described in patent application FR-A-2,607,507, the LNAs such as phosphorothioate-LNA and 2'-thio-LNA described in Bioorganic & Medicinal Chemistry Letters, Volume 8, Issue 16, Aug. 18, 1998, pages 2219-2222, and the PNAs that are the subject of the article by M. Egholm et al., J. Am. Chem. Soc. (1992), 114, 1895-1897, are examples of oligonucleotides consisting of nucleotides whose skeleton has been modified.

Visualization of the hybridization reactions may be carried out by any detecting means, such as direct or indirect means.

In the case of direct detection, i.e. without the intermediary of labeling, the hybridization reactions are observed by plasmon resonance or by cyclic voltammetry on an electrode bearing a conductive polymer.

In the case of indirect detection, i.e. via labeling, the labeling may be performed either directly on the target nucleic acids, or via a specific binding partner of said previously labeled nucleic acids.

Specific binding partner of the target nucleic acids means any partner capable of binding to the target nucleic acid, and as examples we may mention nucleic acids, oligonucleotides or polynucleotides and enzyme substrates.

Labeling means fixation of a marker capable of directly or indirectly generating a detectable signal. A non-exhaustive list of these markers consists of: enzymes that produce a signal that is detectable for example by electrochemistry, colorimetry, fluorescence, luminescence, enzymes such as horseradish peroxidase (HRP), alkaline phosphatase (ALP), beta-galactosidase, glucose-6-phosphate dehydrogenase; enzyme inhibitors; enzyme co-factors; particles such as gold particles, magnetic latices, liposomes; chromophores such as luminescent compounds, dyes, radioactive molecules such as $^{32}P$, $^{35}S$ or $^{125}I$, fluorescent molecules such as fluorescein, rhodamine, the Alexa®, umbelliferone, luminol or the phycocyanins. In the case of fluorescence, it may be the fluorescent product of an enzyme-substrate reaction, a fluorophore-quencher combination, extinction of fluorescence or any other system based on fluorescence properties.

Indirect systems may also be used, for example via another ligand/antiligand pair. Ligand/antiligand pairs are well known by a person skilled in the art, and we may mention for example the following pairs: biotin/streptavidin, sugar/lectin, polynucleotide/complementary polynucleotide. In this case, it is the ligand that bears the binding agent. The antiligand may be detectable directly by the markers described in the preceding paragraph or may itself be detectable by a ligand/antiligand.

These indirect detection systems may lead, in certain conditions, to amplification of the signal. This technique for signal amplification is well known by a person skilled in the art, and reference may be made to the applicant's earlier patent applications FR-A-2 781 802 and WO-A-95/08000 or to the article J. Histochem. Cytochem. 45: 481-491, 1997.

Preliminary labeling of the target nucleic acids may be carried out by direct or indirect incorporation of a marker by a polymerase, by a kinase, randomly or specifically, at the ends or by incorporation "inside" the molecule.

Labeling of the specific binding partners of the target analytes is well known by a person skilled in the art and is described for example by Greg T. Hermanson in Bioconjugate Techniques, 1996, Academic Press Inc, 525B Street, San Diego, Calif. 92101 USA.

Depending on the type of labeling of the conjugate used, for example using an enzyme, a person skilled in the art will add reagents for visualization of the labeling. This step corresponds to development. It is preceded by the use of a washing buffer that makes it possible to remove the fractions of analytes or of elements not used in the reaction, or bound weakly or nonspecifically, in order to limit the background noise.

The aims and advantages of the device according to the present invention will be better understood in light of the following example, not in any way limiting, referring to the figures, in which.

Figure 5A:
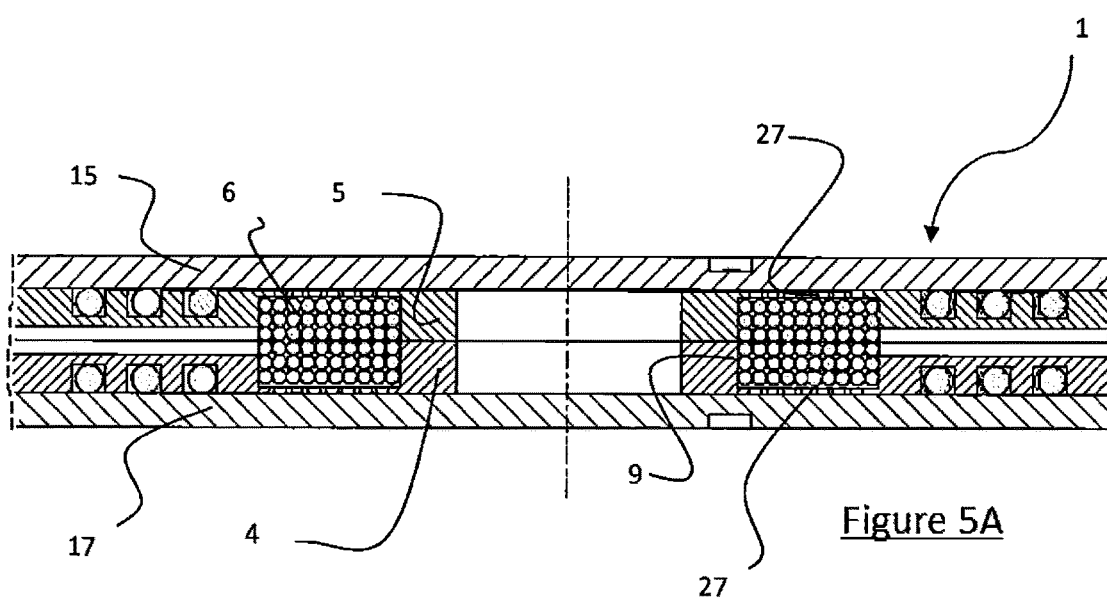
FIG. 5A is a flowsheet of the filtering part of the main card where the beads are present when the confining plates are closed.
Figure 5B:
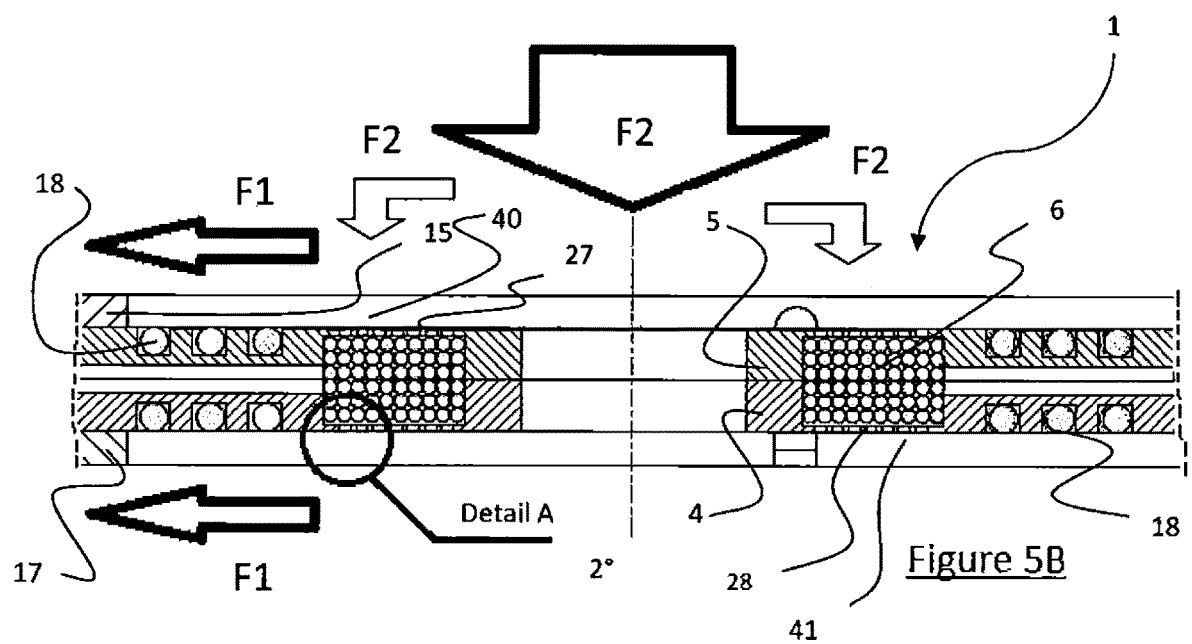
FIG. 5B is a flowsheet similar to that of FIG. 5A, but in which the confining plates are open.
Figure 6:
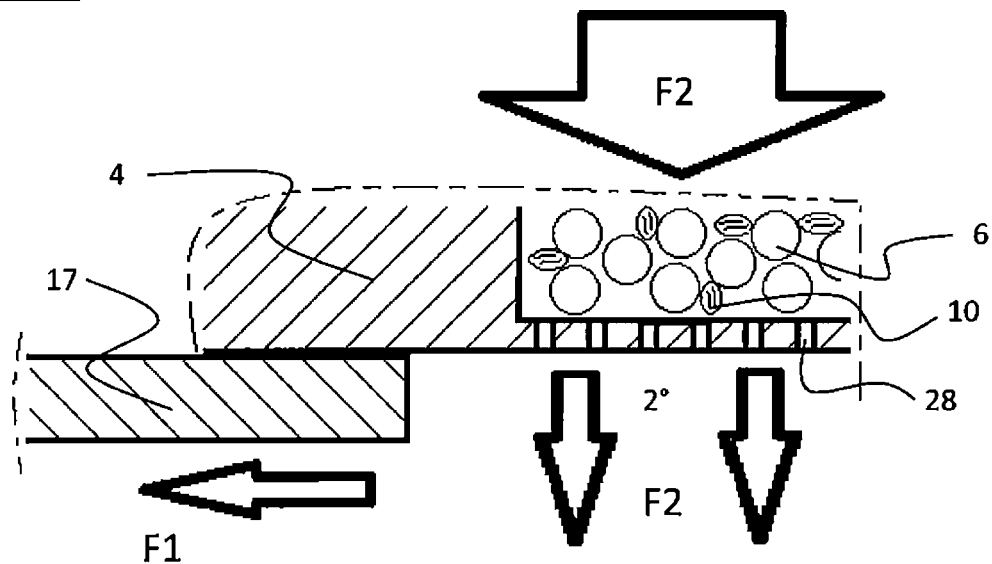

FIG. 6 gives a detail A from FIG. 5B but in which the movement of the fluid within the capture beads and the movement of the confining plates are highlighted.

Figure 7:
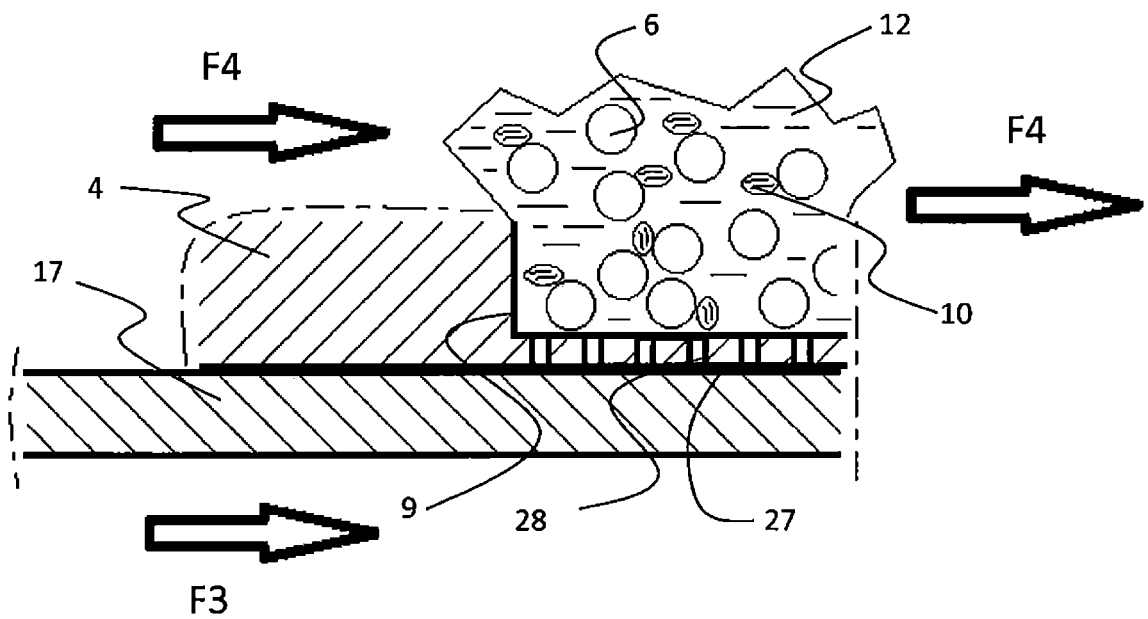

FIG. 7 is identical to FIG. 6 but focuses on the new movement of the confining plates and the start of movement of the reaction liquid within the capture beads.

Figure 8:
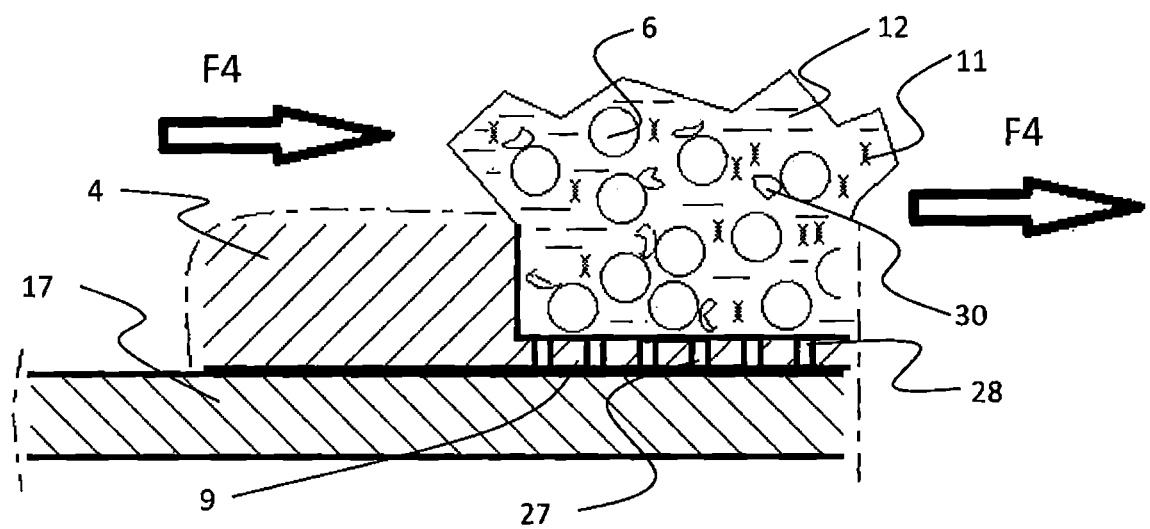

FIG. 8 is identical to FIG. 7 and clearly shows the movement of the fluid within said capture beads.

Figure 9:
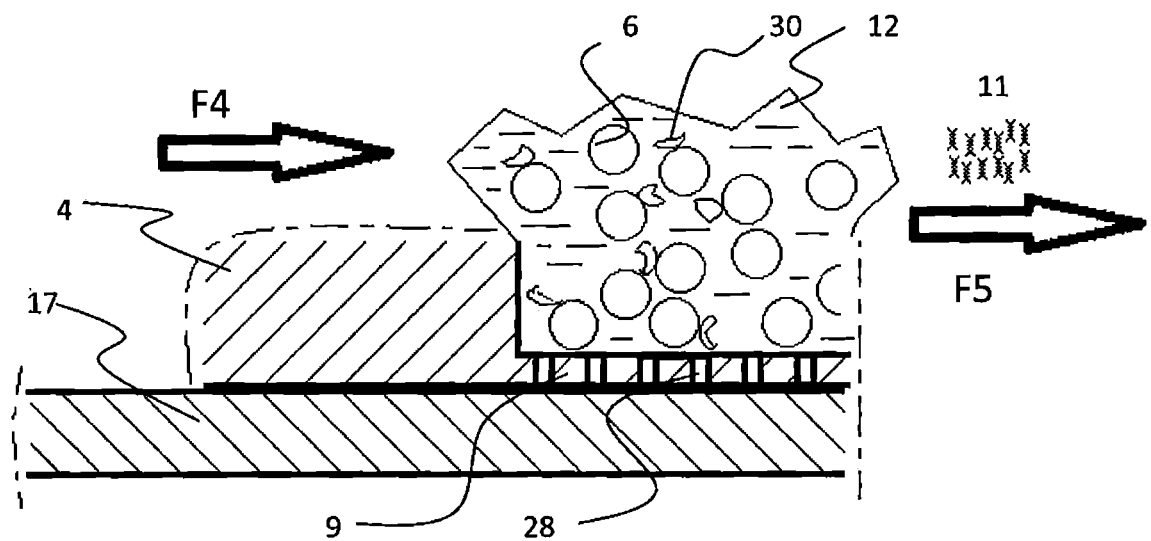
Figures 10A, 10B, 10C, 10D:
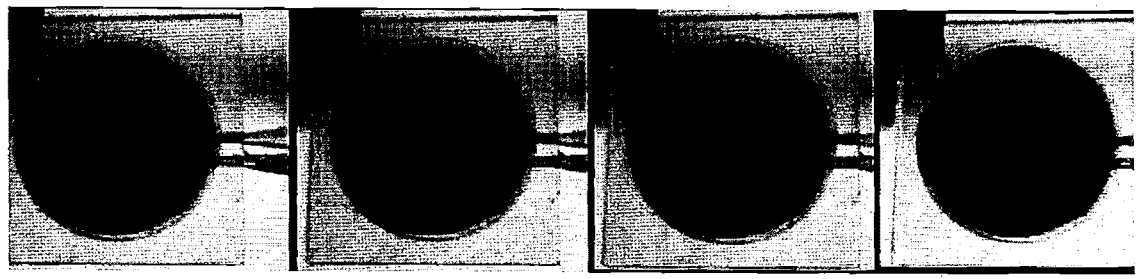

FIG. 9 is identical to FIG. 8 but emphasizes the extraction of the nucleic acids.

FIGS. 10A to 10D show the effectiveness of filling of the chamber where the microorganisms are retained by the retaining means over the course of time.

Figure 11:
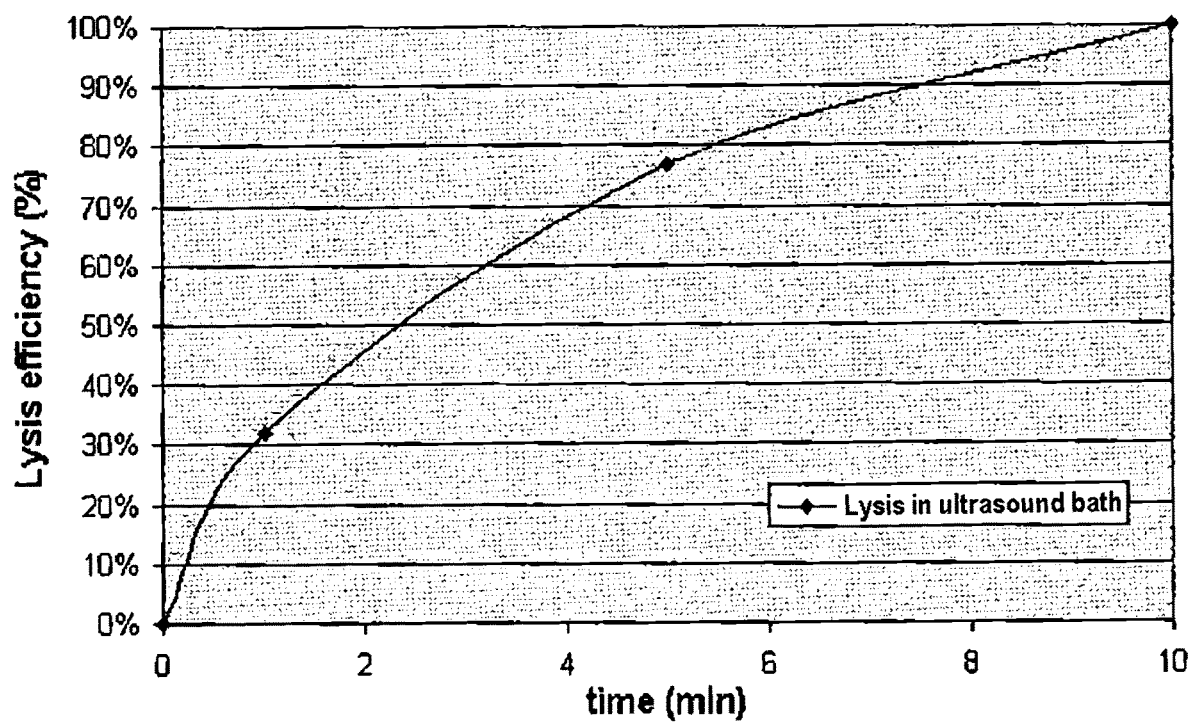

FIG. 11 shows a graph demonstrating the efficiency of lysis within a device according to the invention.

Figure 1:
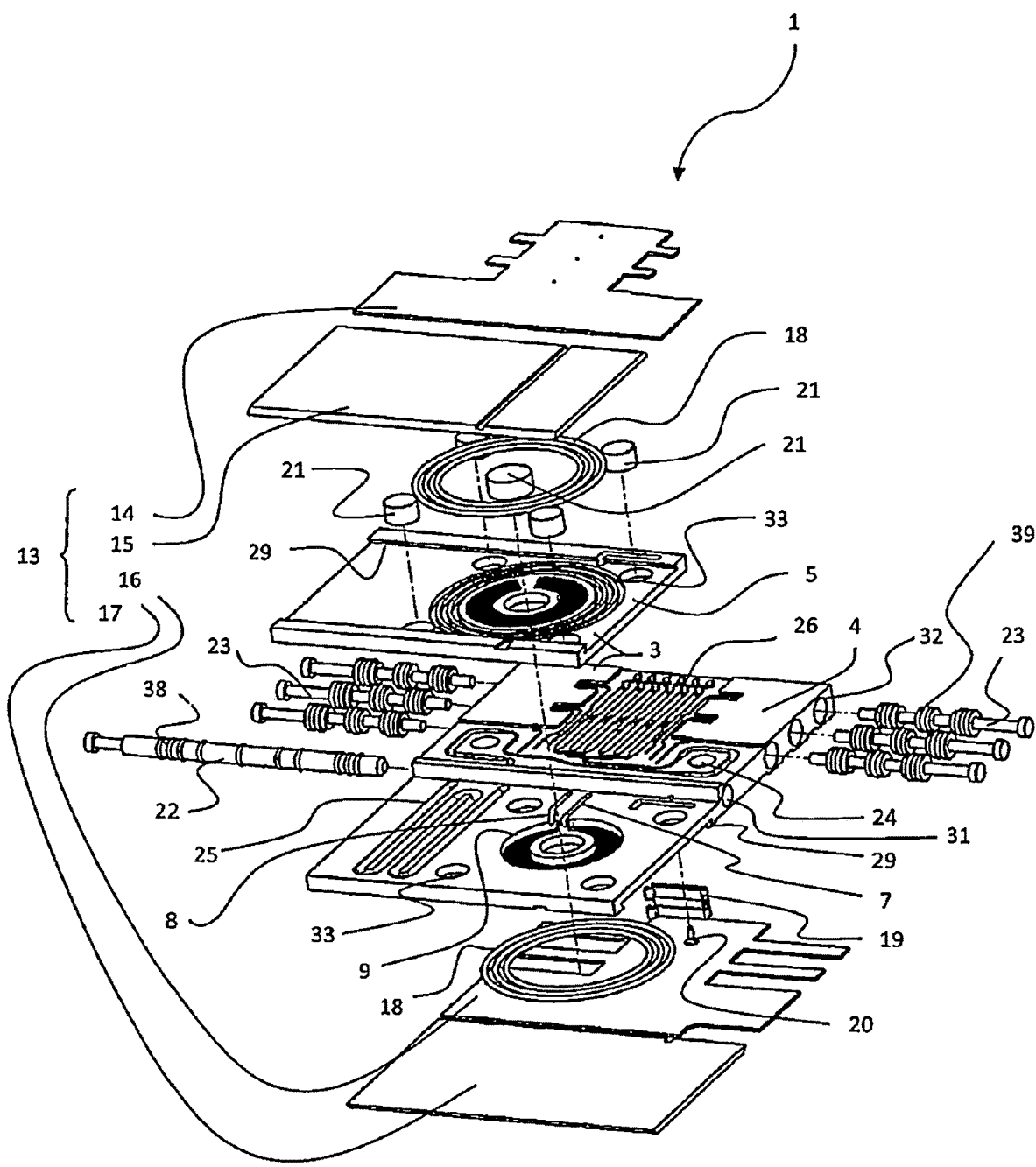
FIG. 1 shows an exploded top view of the card or cartridge used for collecting and lysing the microorganisms with all the elements that allow it to function, according to a particular embodiment of the invention.

The present invention relates to a microorganism collecting device 1. FIG. 1 shows an exploded view of one embodiment presented by the applicant in which the microorganism collecting device 1 is presented without the presence of any fluid 2 or liquid 12. Said collecting device 1 essentially comprises two main parts, a main card 4 positioned in a lower position relative to a secondary card 5, which is in an upper position. The main card 4 is L-shaped, and the secondary card 5 is integrated in this "L" shape to give a general parallelepipedal shape. The main card 4 and secondary card 5 are intended to be brought into contact with one another. In this way they will form a means 9 for retaining beads 6, essentially consisting of a cavity present in the horizontal portion of the "L" shape, this cavity 9 being closed by the bottom face of the secondary card 5 in contact with card 4. The two cards, the main card 4 and the secondary card 5, once assembled form the reaction module 3. However, the retaining means 9 does not simply consist of the edges of this reaction module 3 but also comprises one or more grids 27, not shown in FIG. 1, allowing passage of fluid 2 or liquids 12 but without allowing the beads 6, also not shown, to leave the reaction module 3. On the grid 27, shown in FIG. 4, the diameter of the holes 28 in the grid 27 depends on the diameter of the beads 6 used. The holes 28 in the grid 27 must be of smaller diameter than the diameter of the glass beads. In a preferred embodiment, the holes 28 in the grid 27 must be of significantly smaller diameter than the diameter of the glass beads, "significantly" meaning for example that the beads 6 have a diameter from 400 to 600 μm and that the grid 27 has holes 28 from 200 to 250 μm.

Figure 4:
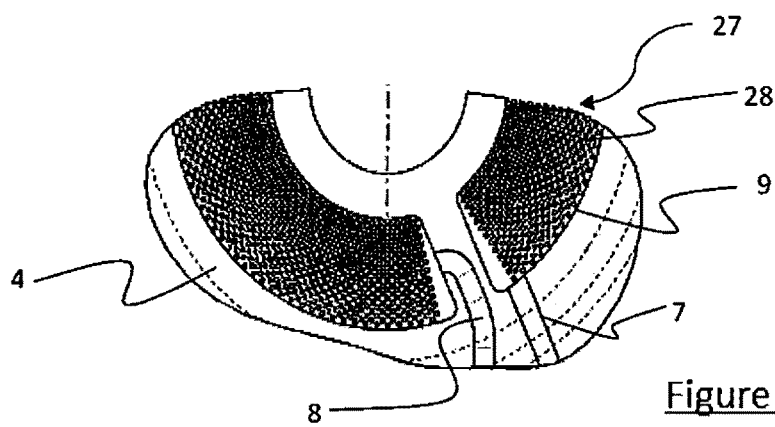
FIG. 4 shows a detail of FIG. 2 at the level of the bed of beads and grid retaining them in the plane in contact with at least one fluid admission duct and allowing capture of the microorganisms. The two opposite ends of the C-shaped module are connected fluidically to the channels for admitting and evacuating the reaction liquid.

The assembly of the two cards 4 and 5 as well as the ducts for admission and evacuation of the fluid 40 and 41 and channels for admitting and evacuating the reaction liquid 7 and 8, shown in FIG. 4, is confined using an airtight confinement enclosure 13, which consists, in the embodiment presented in FIG. 1, of a certain number of confining plates.

Firstly, in an upper position, there are two top plates 14 and 15. Then in a lower position there are two bottom plates 16 and 17; plates 14 and 16 provide confinement of the reaction module 3 notably at the level of the fluidic channels of the analysis zone 26, which will be described later. Then there are the top and bottom ferromagnetic confining plates 15 and 17, which for their part are positioned above said reaction module 3.

After the capture step, plates 15 and 17 are repositioned to close the consumable. Only the microorganisms 10 remain in the chamber 9. Channels 7 and 8 are then used for circulating the elution buffer before the ultrasonic lysis step.

It should be noted that the top plate 15 and the bottom plate 17 are of a ferromagnetic nature as they enclose a certain number of magnets 21 positioned at the four corners of the reaction module 3 as well as at its center. The magnets 21 provide, on the one hand, pressure of the ferromagnetic plates 15 and 17 on the O-ring seals 18 and, on the other hand, hermeticity after capture of the microorganisms. These plates 15 and 17 provide access to the capture beads 6, and make it possible to capture the microorganisms 10 present in the fluid 2 on the beads 6. Plates 15 and 17 slide over the surface of the device 1 on slides 29, located on the sides, and in the present case they are of dovetail shape. On completion of air sampling, said plates 15 and 17 are repositioned to their original location by sliding along the slides 29. The liquid circuit is then closed. A "clamping" force is required on the plates in order to ensure perfect hermeticity on closure. This force is for example ferromagnetic, which has the advantage of being a uniform pressure force on the entire surface of the plates in question.

Between the main card 4 and secondary card 5 and the top plate 15 and bottom plate 17, hermeticity is ensured by a set of hermetic O-ring seals 18. These O-ring seals 18 are three in number in the upper position and three in the lower position and are concentric. Of course, this number is not in any way limiting since the use of a single O-ring seal may suffice. Moreover, other sealing means exist between the top plate 14 and bottom plate 16 and the rest of the device 1. The means employed are notably gluing of each of these plates with a glue or a double-sided adhesive on the main card 4. Similarly, the secondary card 5 is glued permanently on the body 4 of the device. This gluing is performed ultrasonically, by laser or thermally, it is permanent and allows assembly of the collecting device 1.

It should be noted that the main card 4 comprises two zones where there are channels. Firstly there is a storage zone referenced 25 near the reaction module 3. There is also an analysis zone 26, which was mentioned above. The various channels present at the level of zones 25 and 26 allow fluidic management of the whole card. The channel in the storage zone 25 is the reservoir for storage of the reaction liquid 12 (elution buffer). The channels in the analysis zone 26 are the fluidic channels for sample preparation for analysis. They circulate on the front and back of the card. Fluorescence reading also takes place in the channels in zone 26. Since these zones 25 and 26 are not the essence of the invention, they will not be described further.

These types of channels and their functions are better explained in a previous patent application WO-A-2011/033231 filed by the applicant under French priority of Sep. 18, 2009. The reader is invited to refer to this for fuller information.

After capture of the microorganisms 10, plates 15 and 17 are closed again. The buffer from chamber 25 is sent into the capture chamber 9 for resuspending the microorganisms. Then ultrasonic lysis is carried out in this same chamber 9 by a means external to the card. The lysate is then shared via the distributor valve 22, which slides in the hole 31, and is sent into the channels of zone 26 by means of the pump pistons 23, which slide in holes 32, for preparation for detection and amplification of the nucleic acids 11.

However, it should be understood that various elements allow fluidic management and transfer of the reaction liquid 12 from compartment to compartment through the intervention of the distributor valve 22, as well as the pump pistons 23. Three of these pump pistons 23 are on the left of the main card 4, and the other three are on the right of this same card 4.

Finally, to finish the description of FIG. 1, it is noted that there are desiccating stations 24, still within the main card 4. These stations 24 are located near the analysis zone 26, and contain drying agents for optimizing storage of the reagents integrated with the card in the form of beads of lyophilized reagent, also called "pellets", obtained by lyophilization, by drying or else by gelation. The drying agents are not in direct contact with but are close to the pellets. These pellets contain the reagents necessary for amplification of the nucleic acids 11.

The distributor valve 22 controls the distribution of the fluids in the collecting device 1. Accordingly, there are several positions, which provide:
storage of the reaction liquid 12,
transfer of the reaction liquid 12 to the chamber or retaining means 9 containing the beads 6 (after capture of the microorganisms 10),
transfer of a total volume of 120 µl of the lysate, or 20 µl per channel, to the six channels of zone 26.

Finally, the pump pistons 23 are similar to syringes and allow aspiration and transfer of the reaction liquid 12 throughout the process. Their particular feature is that they function in a closed air cycle (no air is aspirated from the exterior), although a simpler version with aspiration of external air is conceivable. The benefit of this closed vessel is maximum avoidance of communication with the exterior and thus risk of cross contamination from the interior to the exterior and vice versa.

It can be seen in FIG. 1 that there is a spring plate 19 for locking the ferromagnetic plates 15 and 17. This plate 19 is attached to the reaction module 3 by a screw 20. Thus, it should not be possible to manipulate these detachable plates unintentionally. This spring plate 19 makes it possible to block and prevent unintended opening of them.

Figure 2:
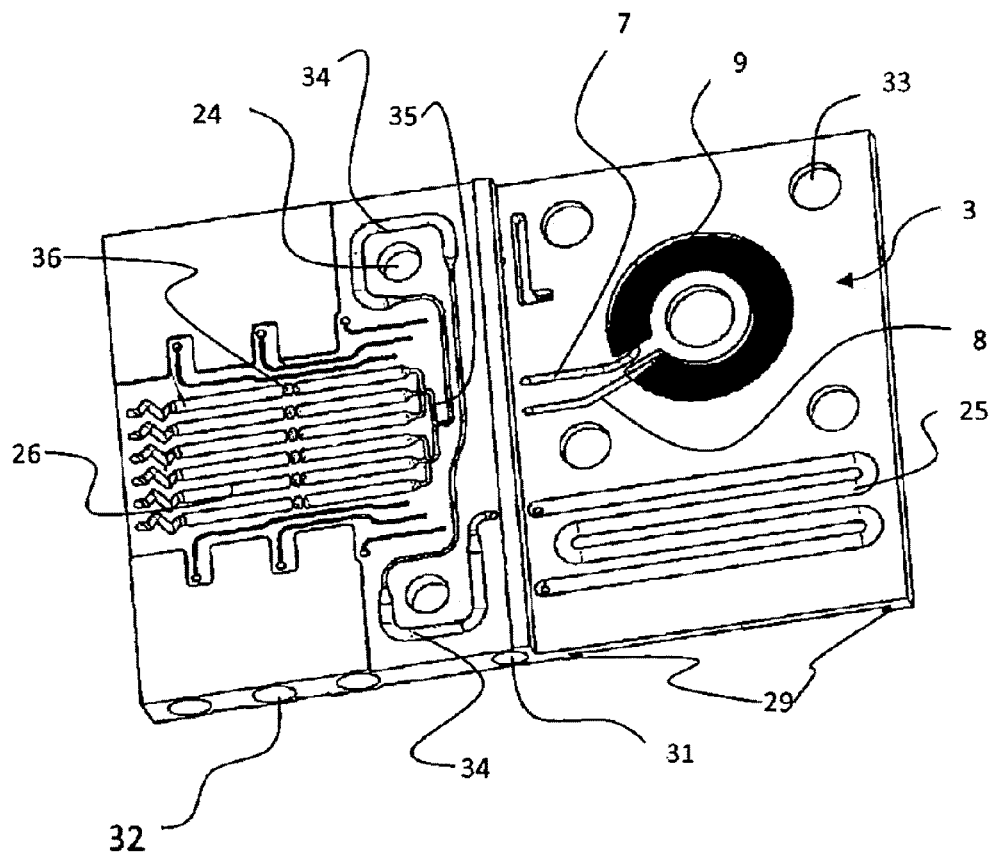
FIG. 2 shows a perspective top view of the main card forming the core of the device according to the embodiment of the invention shown in FIG. 1.

FIG. 2 shows a more detailed view of the main card 4. The latter consists of two portions of different thickness; on the left the thickness is greater and comprises the analysis zone 26. We also note the presence of the drying stations 24, as well as a hole 31 for receiving the distributor valve 22, which is not shown in this figure. Finally there are also six holes 32 for receiving the six pump pistons 23, also not shown in this figure, within the main card 4. On the portion with small thickness of the main card 4, i.e. on the right of this figure, we note the presence of the storage zone 25 for the reaction liquid 12, after said reaction liquid 12 has:
resuspended the captured microorganisms 10,
provided lysis through ultrasonic agitation of the beads 6 via this liquid 12,
transported the organisms of interest, and
finally supplied the reaction mixture 12 necessary for amplification and detection of the nucleic acids 11.

Figure 3:
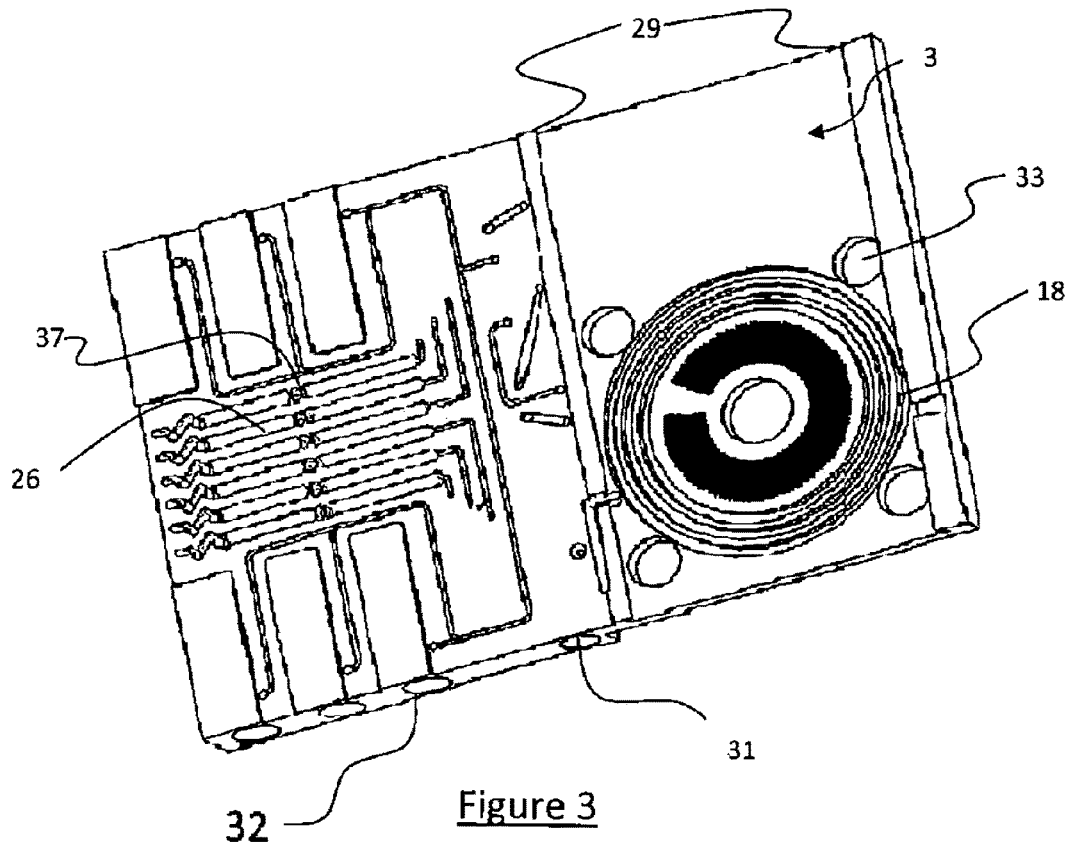
FIG. 3 shows a perspective bottom view of the main card, still according to the embodiment of the invention shown in FIG. 1.

FIG. 3 shows the secondary card 4. It is noted that on this portion there are locations for receiving the O-ring seals 18 as well as locations 33 for receiving the magnets 21; seals 18 and magnets 21 are not shown in this figure.

FIG. 4 shows an enlarged view of a detail of FIG. 2, at the level of the retaining means 9 of the beads 6 as well as channels 7 and 8. The two opposite ends of the C-shaped module are connected fluidically to the channels for admitting and evacuating the reaction liquid 7 and 8.

In the present case, the means 9 consists of a grid 27, shown more clearly in FIG. 5A or 5B. It is noted that the space separating the holes 28 of the grid 27 is small; for example for beads of 500 µm, the holes will have a diameter from 200 to 300 µm and will be separated from one another by spaces of 200 to 300 µm, which leads to the fluids 2 or liquids 12 being forced into this space, which improves and increases the points of contact between the microorganisms, containing the nucleic acids of interest, and the surface of the beads 6 allowing better capture of said nucleic acids 11. The beads 6 are also coated with a substance that further facilitates adhesion of the microorganisms on the surface of the beads. This substance is notably glycerol in the case when the fluid used is a gas. Thus, the use of glycerol only functions in the case of collecting microorganisms in a gas, notably air. In this instance, the air passes over the glycerol and the microorganisms are captured on the latter. The glycerol is then dissolved by the reaction buffer 12. If bacteria are present, they will then be lysed in this buffer by ultrasound. When collecting microorganisms present in water, this does not function with glycerol, which is dissolved by water, and is driven out of the card. To achieve correct operation with a liquid medium, a replacement must be found for glycerol, for example a polymer coating that does not dissolve in water but only in a specific reaction buffer or allows "salting out" in this specific buffer, or a filter may be added downstream of the beads so that the fluid comes into contact with the beads before circulating through the filter.

According to FIGS. 5A and 5B, at the level of the main card 4, with the chamber or retaining means 9, it is noted that there are two ducts referenced 40 and 41. Duct 40 allows admission of fluid 2 into the module 3, said fluid 2 containing the bacteria to be captured for subsequent analysis, whereas duct 41 allows evacuation of this same fluid 2 to the exterior of said module 3. Of course, between admission and evacuation, the fluid 2 will be passed through the module 3 where the beads 6 are present; it is at this level that collection of the microorganisms can be performed. If the fluid 2 is introduced and evacuated via ducts 40 and 41, the reaction liquid 12, which may consist of an elution buffer or other buffer, is introduced via an admission channel 7 into module 3, shown in FIG. 4, it is also evacuated from this same module 3 via an evacuating channel 8, also shown in FIG. 44.

In fact this fluid 2, for example air, but it may also be a liquid different from the reaction liquid 12, circulates perpendicularly to the card. It flows through the grids 27.

FIGS. 5 to 8 give a simplified description of the protocol for capture of a microorganism.

FIG. 5A describes a portion of the device 1 according to the invention, at the level of treatment of the fluid 2, from which we wish to extract the microorganisms 10, in which there are:
- beads 6 present in the cavity, forming retaining means 9,
- an upper grid and a lower grid 27, perforated by several holes 28, which confine the beads 6 within the device 1 and therefore the retaining means 9 of the card 4,
- a ferromagnetic top plate for confinement 15,
- a ferromagnetic bottom plate for confinement 17, plates 15 and 17 not being glued to card 4 like the top and bottom plates for confinement 14 and 16.
- the fluidic channel, not shown in this figure. According to FIG. 5B, device 1 is more or less identical to the configuration in FIG. 5A, but the ferromagnetic top plate for confinement 15 and the ferromagnetic bottom plate for confinement 17 are translated along F1. This allows the fluid 2 to pass, according to F2, into the beads 6, held in position by the grids 27, by a movement perpendicular to the channels for the reaction liquid or liquids, not shown in the figure. This movement is performed via the admission duct 40 and evacuating duct 41 of the fluid 2 within module 3.

FIG. 6 shows detail A from FIG. 5B. In this configuration, the detachable confining plates 15 and 17 are removed according to F1, and the fluid 2 circulates perpendicularly to the axis of the grids 27. The microorganisms 10 are captured on the beads 6 within the retaining means 9.

In FIG. 7, the detachable plates 15 and 17 are returned to the closed position by a sliding motion according to F3. The elution buffer 12 is introduced into the chamber 9 via the admission channel 7. It detaches the microorganisms 10 from the beads 6.

Finally in FIG. 8, once the chamber 9 is full, ultrasonic lysis is carried out to disrupt the microorganisms, for example bacteria, 10 and release the nucleic acids 11. The lysate containing the nucleic acids 11 is sent in the channels via the evacuating channel 8, for preparing amplification by resuspending the beads of lyophilized reagent, by optical detection, etc.

The device therefore makes it possible to capture the microorganisms 10 notably from the air on glycerol-coated glass beads by circulating the air stream through a bed of beads 6.

Capture of microorganisms by means of a dry surface offers many advantages, such as:
- absence of wear of the medium during capture (due to evaporation),
- no evaporation during storage,
- very high concentration of the microorganisms,
- very large developed capture surface (due to the microbeads) relative to a flat impacting surface,
- the capture surface does not saturate so easily, capture is therefore much more efficient than in an impaction system.

Moreover, the device is designed to:
- offer a large surface area out of plane for capture of the microorganisms from the fluid.
- reduce the head losses and therefore the overall dimensions of the pump; thus, during capture of airborne microorganisms, the device is connected to a pump that takes in air through the capture grid 27.
- allow the microorganisms to be taken up in any liquid buffer simply by pipetting owing to the use of fluidic channels in the capture plane; thus, after capture of the microorganisms on the glycerol, the detachable plates 15 and 17 are closed again. The resuspension buffer (stored in chamber 25) is forced into the chamber containing the beads. The microorganisms are then taken in the glycerol; the latter dissolves in the buffer, so that the microorganisms captured are released.
- integrate lysis (notably with ultrasound) in the consumable or device for collecting microorganisms 1,
- obtain a high capture efficiency with a small head loss, as the air passes over a bed of glycerol-coated beads (and is not impacted on a bed of beads).

The capture efficiency largely depends on the thickness of the bed of beads and the size of the beads, but the capture efficiency is significantly higher with capture in transmission through the beads, notably for particle sizes under 1 µm. This capture mode presents technical difficulties, such as:
- control of the head loss,
- keeping the beads in the capture chamber,
- taking up the microorganisms in a buffer,
- lysis.

Dry capture is performed without bubbling or aqueous gel, without loss of efficiency over time (>4 $m^3$ sample). The advantage of glycerol is that it does not dry out. Accordingly, the volume of air sampled can be very large, without notable loss of efficiency. Systems with capture on aqueous surfaces (agar, Petri dish) or aqueous liquid (Coriolis type) have the drawback of drying out as capture proceeds. This drying causes a decrease in capture efficiency. Capture in one defined liquid determines the type of analysis performed downstream of collection whereas with dry capture the microorganisms may be taken up in any buffer.

Moreover, capture on a dry surface (glass beads+glycerol) allows the microorganisms to be released in a very small volume of buffer, less than 1 mL or even less than 100 µL. The advantage of increasing the concentration of the microorganisms is that it promotes detection of them. The systems for detection in molecular biology have a limit of detection of the order of 1 genome equivalent per microliter (µL).

With the conventional devices, it is therefore necessary to capture a far larger quantity (from 15 to 30 times more, i.e. from 200 to 600 µL) of microorganisms as the capture volume is 15 mL (large volume that dilutes the microorganisms).

Mechanical lysis is very effective and is compatible with all types of biological methods, such as ultrasonic lysis in any buffer required for the next steps of the protocol.

Lysis of the captured microorganisms is integrated in the device. The lysis technique is purely mechanical (in contrast to chemical lysis) and, thus ensures an excellent lysis yield, regardless of the lysis buffer selected and the microorganism to be lysed.

It is thus possible to use the lysate as it is, and then carry out amplification, for example NASBA or PCR.

According to a preferred use of device 1 proposed by the invention, after the microorganisms 10 have been lysed and the nucleic acids 11 have been taken up in the reaction liquid or elution buffer 12, the collecting device 1 makes it possible to perform amplification as well as detection of said extracted nucleic acids 11. For this purpose, there are mainly four steps that are carried out after lysis.

The first step consists of extracting the buffer 12 containing the nucleic acids 11 as well as a certain number of residues 30 of microorganisms 10, which are present in the liquid 12 after lysis, these residues not being taken into account subsequently in the analyses that will be carried out at the level of the analysis zone 26. In this first step, the liquid 12 laden with the nucleic acids 11 and the residues 30 will exit from the retaining means 9 via the evacuating channel 8. At the level of the evacuating channel 8, it is for example possible to have a filter that only allows biological elements to pass that have a size less than or equal to the nucleic acids extracted.

In a second step this mixture is sent into a zone for taking aliquots 34, as clearly shown in FIG. 2. The volume thus obtained corresponds to 120 µl.

This aliquot is then sent to a third step in a lysate separation zone referenced 35. In this figure, there are six zones that are well differentiated from one another to allow separation in six times 20 µl in the analysis channels of zone 26. In these channels of zone 26, amplification is carried out, by means of reagents for amplification, such as nucleotides, amplification primers and detection probes, which are positioned in the intermediate zone 36. It can be seen from FIG. 3 that there is a second intermediate zone 37 containing at least one enzyme (one enzyme if carrying out PCR, two if carrying out TMA and three if carrying out NASBA), which is located on the front of the main card 4.

The fourth and last step takes place at the level of the channels of zone 26, as is clearly shown in FIG. 3 to the right of the intermediate zone 37 where detection may be performed.

All of these movements are therefore performed by means of the distributor valve 22 and the pump pistons 23, which by their sliding motion, not shown in the figures, make it possible to direct the liquid from the various zones to other zones that will allow amplification of the nucleic acids 11 and their subsequent detection. The distributor valve 22 and the pump pistons 23 possess seals, clearly shown in FIGS. 1, 38 and 39 respectively, which ensure hermeticity of the system.

Example 1: Efficiency of Capture of Microorganisms (with a Particle Counter) as a Function of Bead Size and Thickness of the Bed of Beads For one and the same device, here is the protocol for capture efficiency as a function of bead size and thickness of the bed of beads.

1.A. Procedure:

The sliding plates 15 and 17 are open throughout the experiment. For this experiment, a particle counter is used which evaluates the quantity of particles per cubic meter ($m^3$) of aspirated air. The particles detected are classified in different size categories between 0.3 µm, 0.5 µm, 1 µm and 5 µm.

Three cycles of measurements are carried out:
1: Blank reference measurement without the device.
2: Evaluation measurement with the device upstream of the particle counter.
3: A second reference measurement.

1.B. Experiment:

The blank reference measurements are averaged. The capture efficiency is calculated as the ratio of the measurements with and without the device.

The results are shown in Table 1 below:

TABLE 1

Efficiency (in %) of capture of the microorganisms (with a particle counter) as a function of bead size and thickness of the bed of beads

| Bead diameter Thickness of the bed of beads | Particle sizes | | | |
|---|---|---|---|---|
| | 0.3 µm | 0.5 µm | 1 µm | 5 µm |
| 212-300 µm 1.5 mm | 50 | 87 | 95 | 98 |
| 212-300 µm 2.5-3 mm | 65 | 85 | 92 | 95 |
| 425-600 µm 1.5 mm | 18 | 65 | 87 | 95 |
| 425-600 µm 2.5-3 mm | 45 | 85 | 90 | 89 |
| WO-A-2009/001010 | 0 | 20 | 65 | 95 |

1.C. Analysis:

For one and the same device 1, Table 1 shows that the capture efficiency is very effective regardless of the bead size and the thickness of the bed of beads relative to the prior art consisting of the device described in the PCT document. Particles smaller than 0.5 µm do not appear to give a sufficient yield, although it is still far higher than the prior art (minimum 18% yield versus zero). For a size between 0.5 and 5 µm the results are good (always above 65% and even, if we exclude the case at 65%, always above 85%). All the thicknesses of the bed of beads tested are acceptable.

Example 2: Optimization of the Head Loss of Each of the Devices Tested

2.A. Procedure:

Each device is placed on a test bench, allowing the head loss to be measured as a function of the air flow rate. The objective is to find the best compromise between capture efficiency of the device 1 and its head loss. A high head loss signifies high electrical consumption of the sampling device (not favorable for portable applications).

2.B. Experiment:

Table 2 is a table for aiding design of the device for capture of microorganisms. It compares the particle capture efficiency (by size range: 0.5-1 µm, 1-5 µm, 5-25 µm) with the head loss (mbar) of the device. The energy required for pumping a certain volume of air through the device is proportional to the head loss (for one and the same flow rate). For application with a portable pump it is necessary to find a good compromise between the capture efficiency and the head loss (see Table 2).

TABLE 2

Efficiency of capture of microorganisms by particle size ranges and head loss of the device tested (at 50 L/min) as a function of bead size and thickness of the bed of beads

| Bead diameter Thickness of the bed of beads | Particle sizes | | | Head loss (mbar) |
|---|---|---|---|---|
| | 0.5-1 µm | 1-5 µm | 5-25 µm | |
| 212-300 µm 1.5 mm | 75 | 95.5 | 95 | 15 |
| 212-300 µm 2.5-3 mm | 80 | 92 | 95 | 25-30 |
| 425-600 µm 1.5 mm | 56 | 89 | 93 | 6-7 |
| 425-600 µm 2.5-3 mm | 72 | 89 | 88 | 15 |
| WO-A-2009/001010 | 43 | 80 | 94.5 | 6-11 |

2.C. Analysis:

In light of this table and in comparison with patent application WO-A-2009/001010, constituting the prior art, it can be seen that the device according to the invention, regardless of the thickness of the bed of beads and the diameter of the beads used, always gives better performance than the solution proposed by the prior art. Moreover, with beads from 425 to 600 µm and a bed thickness of 1.5 mm, the results are the most efficient for capturing the particles than the device of patent WO-A-2009/001010 for an equivalent head loss.

Example 3: Filling and Emptying the Devices

3.A. Procedure:

Only the chamber 9 of beads 6 is tested. The inlet of the bead chamber (full of beads but without liquid) is connected to a fluidic connector and a pipette. The liquid is forced into the bead chamber until it is full. Once filled, it is emptied in the same way.

3.B. Experiment

FIGS. 10A to 10D show filling of the chamber 9 where the microorganisms 10 are captured. 500 µL is injected at the level of the admission channel 7 and 200 µL is recovered at the level of the evacuating channel 8.

3.C. Results:

Filling takes place perfectly.

Example 4: Lysis of the Microorganisms

4.A. Procedure:

A device 1 consisting of a lysis chamber is filled with a buffer 12 containing *Staphylococcus epidermidis*. The device is subjected to ultrasound, via a sonotrode, in order to lyse the microorganisms. The experiment is repeated with a lysis time of 0, 1, 5 and 10 minutes. The lysis yield is evaluated by growth and counting of the lysates on a Petri dish. The objective of this experiment is to find a suitable interface for transmission of ultrasound in the lysis step.

4.B. Experiment:

In relation to FIG. 11, one and the same design of bead chamber device is used with some interface configurations, i.e.:
- 1st configuration: with plastic elements replacing the ferromagnetic plates 15 and 17 (sonotrode in direct contact with a modified device according to the invention),
- 2nd configuration: with a layer of silicone (present between the sonotrode and the device according to the invention),
- 3rd configuration: with metallic elements serving as ferromagnetic plates 15 and 17 added to the device.

The three devices are tested as before and for two types of bead diameter (see Table 3).

TABLE 3

Efficiency of ultrasonic lysis

| Device | Standard | | Metal insert | | Silicone layer |
|---|---|---|---|---|---|
| Diameter of glass bead (µm) | 212-300 | 425-600 | 212-300 | 425-600 | 212-300 |
| Lysis efficiency (%) | 90-100 | 50 | 100 | 98 | 40-55 |

4.C. Results:

The results are quite good for all of the tests carried out. However, the solution using the metal inserts gives good results that are more or less identical for both types of beads.

Example 5: Lysis and NASBA Amplification without Purification of Microorganisms (*S. epidermidis*)

5.A. Procedure:

A device is filled with buffer containing *S. epidermidis* bacteria as well as an internal control consisting of a bacterium different from the bacterium tested. Lysis is carried out in the device according to the 3rd configuration described in example 4. The lysate is then removed from the device and analyzed.

5.B. Experiment:

The detection curves are presented in Tables 4 and 5 below.

| | Reference (control range) (eq. CFU/µl) | | | | | | |
|---|---|---|---|---|---|---|---|
| | 0 | 0.1 | 1 | 10 | 100 | 1000 | 10000 |
| Result | Negative | Positive | Positive | Positive | Positive | Positive | Positive |

| | Samples tested (eq. CFU/µl) | | | | |
|---|---|---|---|---|---|
| | 0 | 0.2 | 2 | 20 | 200 |
| Result | Negative | Positive | Positive | Positive | Positive |

This experiment shows the efficiency of the device described for lysing the microorganisms and for detecting them by NASBA analysis. The microorganisms are injected into the buffer 12 before the experiment (a different concentration of microorganism in each experiment). The metal flaps of the card are closed. The part containing the beads is filled with buffer 12 (which contains various concentrations of microorganisms). The device is placed on an ultrasound probe to perform lysis. At the end of the lysis step, the buffer 12 is collected manually and analyzed by NASBA away from the card. These results are to be compared with a control range.

By first intention, the interpretation of the results is binary: Positive signifies that there is detection of the microorganism and negative signifies that the microorganism is not detected.

5.C. Analysis:

It can be seen from the above tables that the samples tested are marked as positive for all concentrations above 0.2 CFU/µl.

REFERENCE SYMBOLS

1. Device for collecting microorganisms 10
2. Fluid
3. Reaction module
4. Main card
5. Secondary card
6. Beads
7. Reaction liquid admission channel 12 of module 3
8. Channel for evacuating the reaction liquid 12 from module 3
9. Retaining means of the beads 6 within module 3
10. Microorganisms present in the fluid 2

11. Nucleic acids present in the microorganisms 10
12. Reaction liquid
13. Airtight confinement enclosure consisting of plates 14 to 17
14. Top plate for confinement of device 1
15. Sliding ferromagnetic top plate for confinement of device 1
16. Bottom plate for confinement of device 1
17. Sliding ferromagnetic bottom plate for confinement of device 1
18. Hermetic O-ring seals between the enclosure 13 and the cards 4 and 5
19. Spring plate for locking the ferromagnetic plates 15 and 17
20. Fixing screw of the spring plate 19
21. Magnets
22. Distributor valve
23. Pump pistons
24. Desiccating stations
25. Storage zone of reaction liquid 12
26. Analysis zone on the front and back of the card
27. Upper and lower grids
28. Holes in grid 27
29. Slides
30. Residues of microorganisms present in the liquid 12 after lysis
31. Hole for receiving the distributor valve 22
32. Holes for receiving the pump pistons 23
33. Through-holes of cards 4 and 5 receiving the magnets 21
34. Aliquoting zone
35. Separation zone
36. First intermediate zone containing an enzyme
37. Second intermediate zone containing an enzyme
38. Seals on the distributor valve 22
39. Seals on the pump pistons 23
40. Fluid admission duct 2 within module 3
41. Duct for removing the fluid 2 within module 3
F1. Sliding motion of the ferromagnetic top plate 15 and ferromagnetic bottom plate 17 allowing opening for passage of fluid 2
F2. Movement of fluid 2 passing through beads 6
F3. Sliding motion of the ferromagnetic top plate 15 and ferromagnetic bottom plate 17 allowing closure to passage of liquid 12
F4. Movement of liquid 12 passing through beads 6
F5. Extraction of the nucleic acids 11

The invention claimed is:

1. A method for collecting microorganisms when the microorganisms are contained in a fluid, comprising:
    introducing the fluid into a cavity of a collecting device via at least one admission duct;
    capturing the microorganisms when the microorganisms are contained in the fluid by adhesion of the microorganisms onto surfaces of a set of beads retained in the cavity as the fluid passes through the set of beads;
    evacuating the fluid from the cavity via at least one evacuating duct;
    introducing a reaction liquid into the cavity via at least one admission channel;
    detaching the microorganisms from the surfaces of the set of beads with the reaction liquid as the reaction liquid passes through the set of beads; and
    evacuating the reaction liquid from the cavity via at least one evacuating channel,
    wherein the admission duct is different from the admission channel and the evacuating duct is different from the evacuating channel, and wherein the set of breads includes beads coated with a substance to facilitate the adhesion of the microorganisms onto the surfaces of the set of beads.

2. The method as claimed in claim 1, wherein the admission channel and the evacuating channel and the admission duct and the evacuating duct are positioned as follows:
    the admission duct and the evacuating duct face one another along an axis;
    the admission channel and the evacuating channel are positioned respectively at two opposite ends of the cavity; and
    the admission channel and the evacuating channel are positioned in a plane perpendicular to the axis.

3. The method as claimed in claim 2, wherein the cavity has a "C" shape if the cavity is cut along the plane perpendicular to the axis in which the admission channel and the evacuating channel are positioned, to ensure that the reaction liquid passes completely through the set of beads between a moment when the reaction liquid is admitted to the cavity and a moment when the reaction liquid is evacuated from the cavity.

4. The method as claimed in claim 3, wherein the cavity has a quadrilateral shape if the cavity is cut along a radius passing through the center of the "C" shape and cut[ting] through the "C" shape.

5. The method as claimed in claim 3, wherein the admission channel is connected to one end of the "C" shape of the cavity, and the evacuating channel is connected to the other end of the "C" shape.

6. The method as claimed in claim 1, wherein at least one upper plate and at least one bottom plate of the collecting device [are configured to] close a reaction module including the cavity [to] and form an airtight confinement enclosure in order to isolate the fluid and the reaction liquid from outside of the collecting device.

7. The method as claimed in claim 1, wherein the beads have a diameter in the range from 200 to 600 μm and are retained in the cavity by retaining elements that comprise grids including pores having a diameter smaller than the diameter of the beads and having a diameter in the range from 100 to 500 μm.

8. The method as claimed in claim 1, wherein the fluid is a gas, the set of beads includes beads coated with glycerol, and the reaction liquid liquefies the glycerol upon contacting the reaction liquid to the beads coated with glycerol.

9. The method as claimed in claim 1, wherein the fluid is a liquid and passes through the set of beads and then a filter before it being evacuated from the cavity.

10. The method as claimed in claim 1, wherein the reaction liquid is filtered after it being evacuated from the cavity via the evacuating channel.

11. The method as claimed in claim 1, further comprising agitating the set of beads to mechanically lyse membranes of the microorganisms [in connection with detaching] during a process which the microorganisms are detached from the surfaces of the set of beads.

12. The method as claimed in claim 11, wherein [the beads are agitated] said agitating the set of beads is by ultrasound.

13. The method as claimed in claim 1, further comprising mechanically lysing membranes of the microorganisms to release nucleic acids from the microorganisms and separating the nucleic acids from cellular residues of the microorganisms in the collecting device.

14. The method as claimed in claim 13, further comprising obtaining amplicons by amplifying the nucleic acids [to obtain amplicons] and detecting the amplicons in the collecting device.

\* \* \* \* \*